United States Patent [19]

Wilson et al.

[11] Patent Number: 5,208,747
[45] Date of Patent: May 4, 1993

[54] ULTRASONIC SCANNING METHOD AND APPARATUS FOR GRADING OF LIVE ANIMALS AND ANIMAL CARCASES

[76] Inventors: John Wilson, 96a London Road, Marlborough, Wilts. SN8 2AP, Great Britain; Richard D. Capello, 1911 Rushmore, Orange, Calif. 92667

[21] Appl. No.: 673,164

[22] Filed: Mar. 18, 1991

Related U.S. Application Data

[63] Continuation of Ser. No. 335,114, Apr. 7, 1989.

[30] Foreign Application Priority Data

Apr. 7, 1988 [GB] United Kingdom ............... 8808101

[51] Int. Cl.$^5$ ............................................. A22B 17/00
[52] U.S. Cl. ............................ 364/413.25; 128/660.07
[58] Field of Search ...................... 364/413.19, 413.25; 73/67.8, 597, 602; 128/660.01, 107

[56] References Cited

U.S. PATENT DOCUMENTS

| | | | |
|---|---|---|---|
| 3,964,297 | 6/1976 | Jorgensen et al. | 73/609 |
| 4,138,999 | 2/1979 | Eckhart et al. | 73/597 |
| 4,359,055 | 11/1982 | Carlson | 128/660.07 |
| 4,785,817 | 11/1988 | Stouffer | 73/602 |

FOREIGN PATENT DOCUMENTS 2545010 11/1984 France .

OTHER PUBLICATIONS

Article: Animal Breeding Abstracts by Geoffrey Simm Dec. 1983 pp. 853–875.
Mark's Standard Handbook for Mechanical Engineers, ninth edition, pp. 5-82 and 5-83 (labelled Exhibit A), pp. 12-141 and 12-142 (labeled Exhibit B).

Primary Examiner—Gail O. Hayes
Attorney, Agent, or Firm—Merchant, Gould, Smith, Edell, Welter & Schmidt

[57] ABSTRACT

Ultrasonic scanning of live animals and carcases particularly for grading, which scanning is preferably carried out on live animals to determine expected carcase composition, comprises use of an elongate scanning element along a line parallel to the lie of the spine. The method and apparatus enable data to be obtained for processing to identify thicknesses of the skin/fat layer and the muscle layer there adjacent and also the fat content of the muscle.

12 Claims, 9 Drawing Sheets

ULTRASONIC SCANNING METHOD AND APPARATUS FOR GRADING OF LIVE ANIMALS AND ANIMAL CARCASES

This is a continuation, of application Ser. No. 07/335,114, filed Apr. 7, 1989, now abandoned.

This invention relates to the ultrasonic scanning of live animals and carcases and more particularly to scanning method and scanning apparatus for grading of live animals according to the carcase composition thereof likely to be obtained on slaughter.

Ultrasonic techniques have been used for many years to evaluate the carcase composition of live animals. The precision of predicting a given carcase trait varies widely depending on the type of animal, the ultrasonic machine used, scanning site and operator and interpreter experience and results obtained are often not superior to those obtainable by purely manual techniques. Generally, ultrasonically measured muscle areas have been thought to be the best predictors of dressing percentage, lean: bone ratio and weight of retail cuts, while ultrasonic fat measurements have been the best predictors of lean and fat percentages in the carcase. A summary of techniques hitherto employed is given by G. Simm "Animal Breeding Abstracts", vol. 51, No. 12, pages 853 to 875 which indicate that hitherto scanning has always been at right angles to the spinal cord of the animal either in the ventral-dorsal direction or in the dorso-ventral direction. It has always been the intention of practitioners to build up a picture of the eye muscle to the side of the spinal cord in order to obtain indications which allow the carcase composition of live animals to be predicted.

Subsequent studies carried out by the present inventor have established that such practices are based on a fallacious view compounded by the fact that techniques hitherto employed in carrying out dorso-ventral and ventral-dorsal ultrasonic scans yield results whose interpretation is difficult to carry out with any predictable degree of accuracy as a result particularly of variable compressibility of tissue when proceeding outwardly from the spine and consequential difficulty in achieving reproducible pressure for scanning. The many inaccurate predictions obtained can lead to animals being sent to slaughter which will not possess a muscle: fat weight ratio which will place it in one of the better categories for achieving maximum sales value per animal. In particular, animals may, on slaughter, be found to have too high a fat content to be of any commercial value.

It is thus an object of the invention to provide a method and apparatus for carrying out grading of carcases and more particularly for carrying out grading of live animals using ultrasonic scanning techniques to yield results which will enable the carcase composition of the animal to be evaluated accurately.

According to one aspect of the present invention, there is provided a method of carrying out the ultrasonic scanning of live animals and carcases for determining fat and muscle thickness and/or fat content of muscle, which comprises utilising an elongate ultrasonic scanning element along a line parallel to the lie of the spine.

More particularly, there is provided a method for measuring the fat and muscle thickness of live animals and carcases for the purpose of grading which comprises the steps of:

(1) scanning parallel to the spinous processes of the backbone of the animal over the eye muscle using an ultrasonic scanner;

(2) forming and capturing an image of a selected region thus scanned;

(3) processing said image to identify the thickness of the skin/fat layer and the muscle layer there adjacent and (4) computing a Fat Class to be used as a factor for carcase classification in conjunction with animal weight, age, sex and conformation.

Should it be desired to establish the fat content of muscle, the scan of a representative area of the muscle layer is segmented into regions of similar density and the ratio of low density (darker) areas to higher density (lighter) areas is determined as an indication of the percentage of fatty tissue in the muscle layer. Again a Fat Class can be computed for use in carcase classification which is based on such ratio and takes into account animal, weight, age, sex and conformation. The fatty tissue percentage data can be combined with the Fat Class computed in the aforesaid step (4) to produce an overall animal grade.

According to a second aspect of the invention, there is provided apparatus for carrying out the method of the invention which comprises an ultrasonic scanner of elongate form and a computer operatively associated therewith, the computer being programmed to evaluate the results of scanning for fat and muscle depth and/or fat content of muscle parallel to the spinous processes of an animal and over the eye muscle and compare the results with standard results for like animal weight, age, sex and conformation to provide a grading of the animal in accordance with such evaluation, the computer having associated means for storing and/or for reproducing data received from the scanner and/or for displaying the result of such evaluation.

In one form of this apparatus, the computer is programmed to segment a representative scanned area of muscle into regions of similar density and to compute the ratio of low density (dark) areas to higher density (lighter) areas as an indication of the percentage of fat in the scanned area of muscle to provide a grading of the animal in accordance with such evaluation. Again the computer has associated means for storing and/or reproducing data received from the scanner and/or for displaying the result of such evaluation.

Indeed, both apparatus variants can be combined in a single apparatus, wherein data from both variants is combined to produce an overall animal grade.

The present invention is applicable to the automatic and semi-automatic grading of a wide variety of livestock animals and of carcases obtained therefrom. It is particularly suitable for grading of cattle, sheep and pigs although it is also applicable to the grading of fowls. The principle underlying the invention is a simple one which has nevertheless not been considered hitherto. Indeed, hitherto it has been felt that the more direct readings taken transverse to the spine and accordingly reproducing the profile of the eye muscle would be more satisfactory. It has now been found that by working parallel to the spine, and more particularly along the spinous processes of the backbone where muscle and fat cover is relatively thin, error due to reflections of sound on the one hand and from difficulty in applying the probe with a reproducible pressure to a scanning site are substantially avoided.

When carrying out the method of the invention, it is possible to use a standard ultrasonic scanner provided with an on-board computer. The computer will be programmed to reproduce in visible form, for example as an on-screen display or as a print-out, data received from the scanner. In a more sophisticated form, the computer can also be programmed to utilize such data in a computation of a Fat Class as a means of categorising the type of carcase to be expected from a live animal investigated with the scanner by relating fat/muscle measurements and/or muscle fat content to standard data available in the computer. This will have been obtained by scanning a large number of animals in like manner both before and after slaughter, identifying the quality of carcase after slaughter and seeing how this matches fat/muscle measurements obtained before slaughter. It has been found that such correlation is generally very reliable when scanning has taken place according to the present invention.

When carrying out the method of this invention, the scanner will not generally be applied directly to the back of the animal, but there will be provided a spacer bag therebetween such as is used with autoscopes for scanning the eye. The spacer bag is necessary because placing the ultrasonic probe close to the subject will result in out-of-focus scanning. Maintenance of satisfactory scanning medium between scanner and skin is completed by placing a layer of vegetable oil between the bag and the skin.

Although in principle scanning can take place at any position along the spine, as with the prior art transverse scanning, it is preferable for scanning to take place in the lumbar region. As a preferred form of apparatus embodying the invention, the ultrasonic scanner carries a laterally projecting member extending the size of the spacer bag and having a locating finger hole therein for assisting in determining the amount of pressure to be applied to the bag and obtain a standard muscle thickness on proper location of the probe. This lateral member assists beneficially in ensuring that the same tolerance is always adopted for pivoting of the ultrasonic scanner with the intention that the shortest travel distance between scanner and tissue is attained subject to in-focus scanning being obtained.

By scanning parallel to the line of the spine laterally of the spine over the eye muscle and the tips of the transverse processes formed on the spine, at any position along the spine, there can be obtained on scanning an image of fat and muscle thickness at a particular interval proceeding laterally from the spine. This enables the results of scanning to be represented in terms of gray values, i.e. brightness values at different positions through the scanned region as will be described hereinafter in greater detail with reference to the accompanying drawings.

Thus, a preferred form of apparatus embodying this invention comprises means for reproducing an ultrasonic scan as a visible image and means for optically scanning the visible image at a series of rows extending through the depth of the image, which means is in operative association with the computer which is programmed (a) to determine the mean gray value of the optical scan, (b) to smooth the mean gray value to eliminate high frequency variations, (c) to threshold the data obtained at a value determined by the dynamic range of the smoothed data to produce a binary image, (d) to process the data from the optical image to identify the number of ultrasonically scanned rows spanned by areas of the binary image corresponding either to fat and bone layers or to muscle layers, (e) to compute the depth of said layers from data held by a memory of the computer comprising scan resolution and ultrasonic transducer characteristics and (f) to compare the layer depths against standards attained with carcases as a measure of the grade of animal or carcase ultrasonically scanned.

For a better understanding of the invention and to show how the same can be carried into effect, reference will now be made by way of example only to the accompanying drawings wherein:

FIG. 4(a) is a photograph of the scan obtained typically with the procedure shown in FIGS. 2 and 3a;

FIG. 4(b) is a sketch identifying the features shown in FIG. 4a;

Figures 1A, 1B, 2:
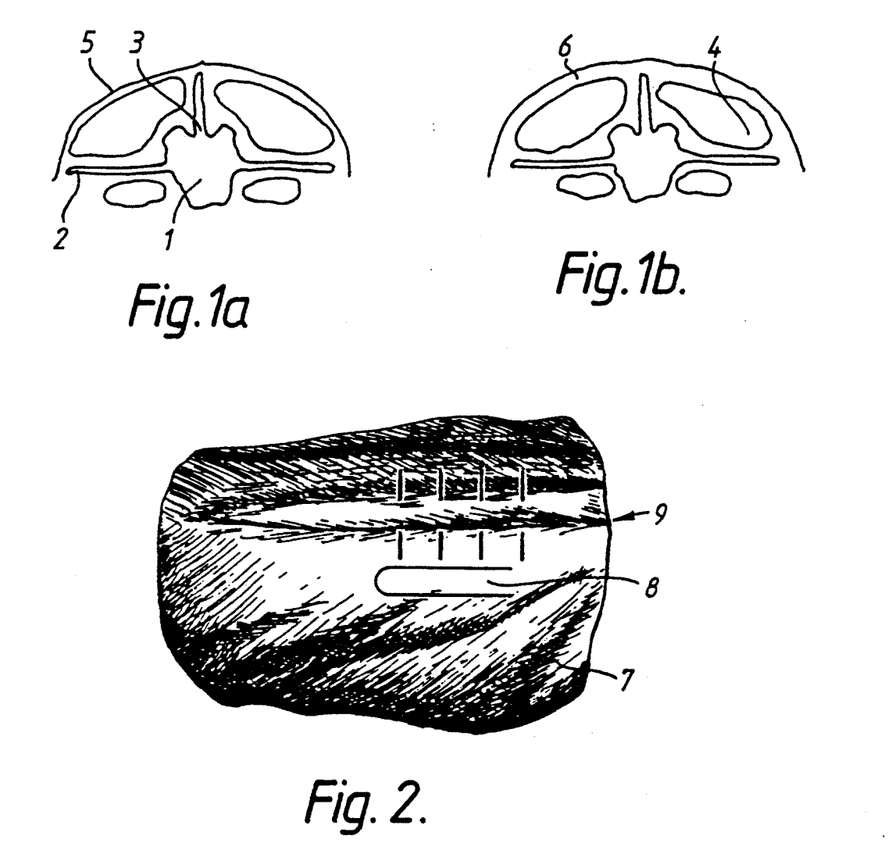
FIGS. 1(a) and 1(b) are schematic tranverse cross-sections through carcases of different fatness.
FIG. 2 is a photograph taken from above showing the position at which scanning may take place on a lamb.

Referring to FIGS. 1a and 1b of the drawings, these are largely identical, differing primarily in the amount of fat tissue to be seen in the transverse section through a carcase in the region of the loin. More specifically, in each case the carcase shows bony material constituted by the spine 1 with transverse process 2 and spinous process 3 projecting therefrom. Laterally of the spinous process are bodies 4 of eye muscle separated from the skin 5 by a layer of fat 6. In FIG. 1a the layer of fat 6 is much thinner than in FIG. 1b and correspondingly there is a much greater body of eye muscle 4. A leaner Low Fat Class carcase of the type shown in FIG. 1a would thus be commercially more valuable than a high Fat Class carcase as shown in FIG. 1b.

Turning next to FIG. 2, there is shown for illustrative purposes a saddle of lamb 7, i.e. lumbar region of a lamb carcase. The carcase 7 is marked to show the position 8 at which scanning is to take place on a live animal by means of an ultrasonic probe, this position being parallel and to the side of the midline 3 of the back of the animal and overlapping the transverse processes of the spine (see FIGS. 1a and 1b).

Figure 3A:
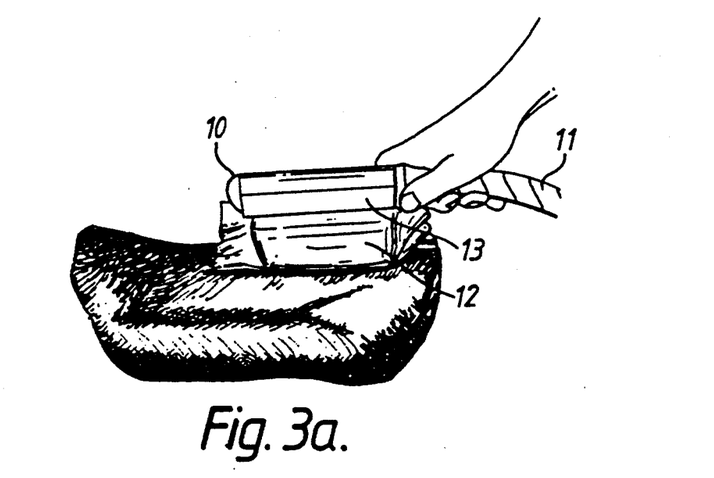
FIG. 3(a) is a photographic side view of an ultrasonic probe in use in a scanning operation.
Figure 3B:
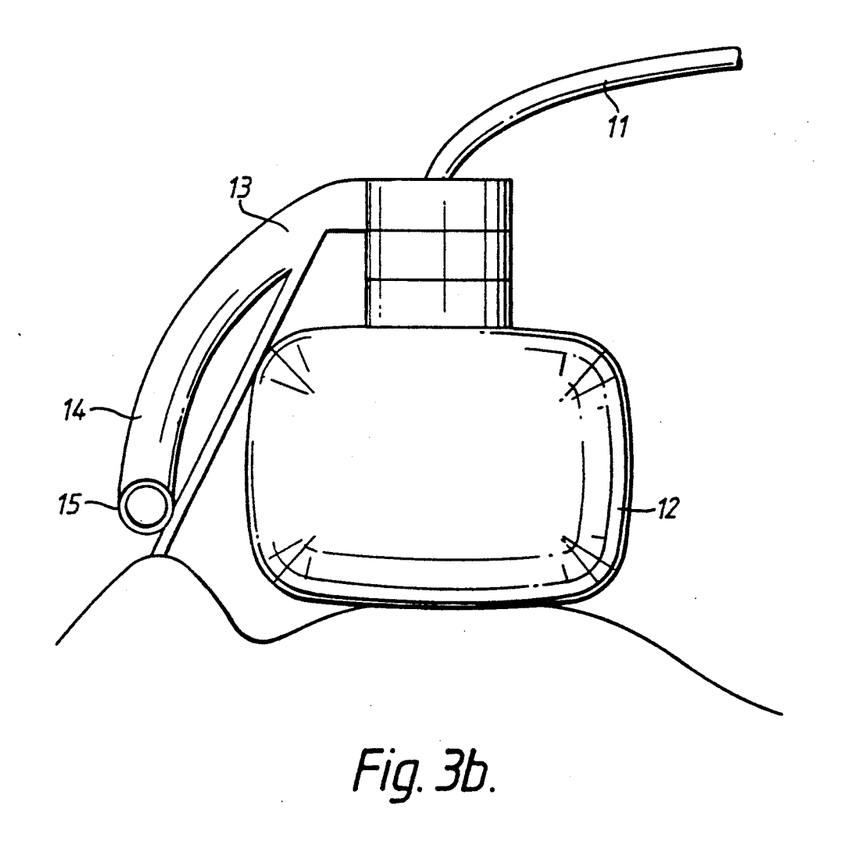
FIG. 3(b) is a sketch of a section at right angles to the view of FIG. 3a showing in detail features shown generally in the former.

FIG. 3a, like FIG. 2 shows a saddle of lamb as a test body. An ultrasonic scanner or probe 10 having a powerline 11 thereto surmounts a fluid filled bag 12 placed to the side of the spine of the saddle of lamb. Attached to the ultrasonic probe is a flanged member 13 for applying pressure to the bag manually, thereby to obtain a desired pressure on the test region when scanning. This member 13 may be modified as shown in tranverse section in FIG. 3b to provide a lower region 14 which is rounded and formed with an opening 15 for location of the finger of the operator. In this way it is possible to get fine control of the location of the probe and ensure that standard muscle thickness is obtained in testing through proper location of the probe. The tolerance of operation is enhanced with the probe being able to pick out the position of shortest distance to muscle tissue.

Figures 4A, 4B:
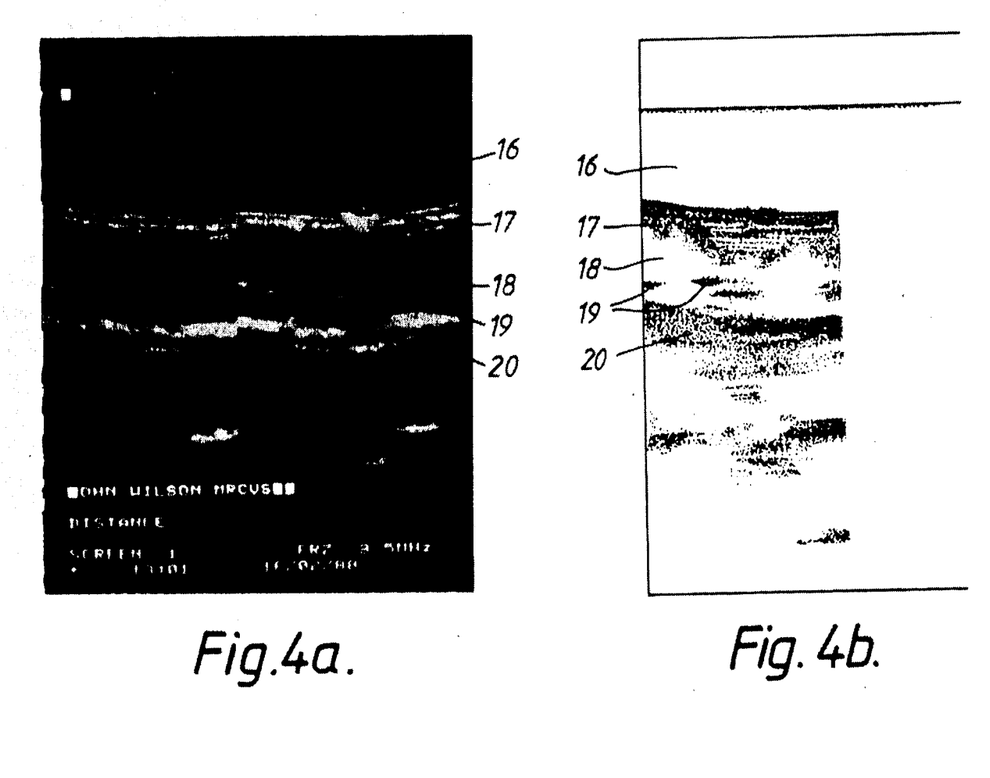

FIG. 4a is a photograph of an ultrasonic scan taken in the manner shown in the preceding figures, that is vertically through the eye muscle parallel to the spine of the animal at a predetermined distance therefrom. The apparent repetition of features is due to reflections at dense regions lower down in the animal and it is only the uppermost features which are of interest. Thus referring to FIG. 4b, these features are identified in a sketch which shows the bag 16 which acts as a stand-off device surmounting a fat layer 17 over a dark region 18. The dark region which corresponds to muscle is interrupted by white areas 19 which are in fact indicative of the position of the ribs. The first reflections appearing below these features is identified by the reference numeral 20.

Figure 5A:
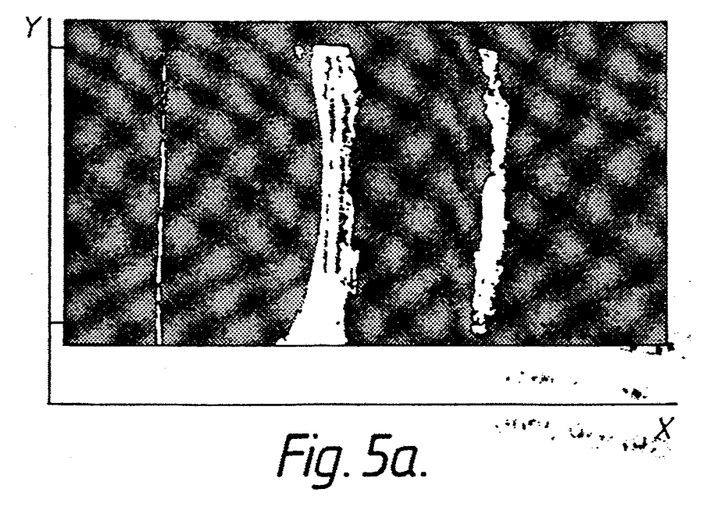
FIGS. 5(a), 5(b) and 5(c) are representative of the processing of the results of ultrasonic scanning taken parallel to the spine of an animal over the eye muscle in the lumbar region thereof.
Figure 5B:
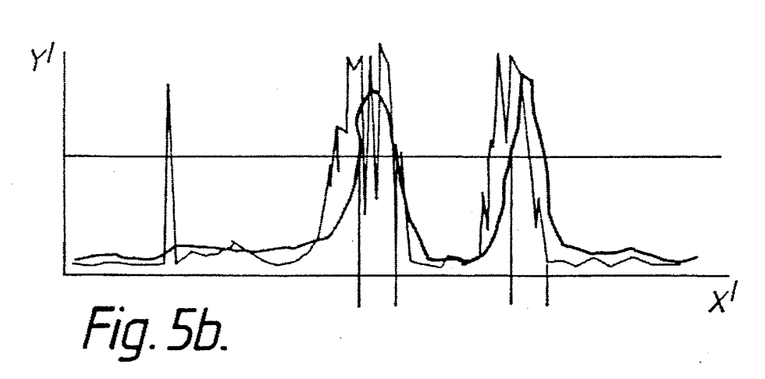
Figure 5C:
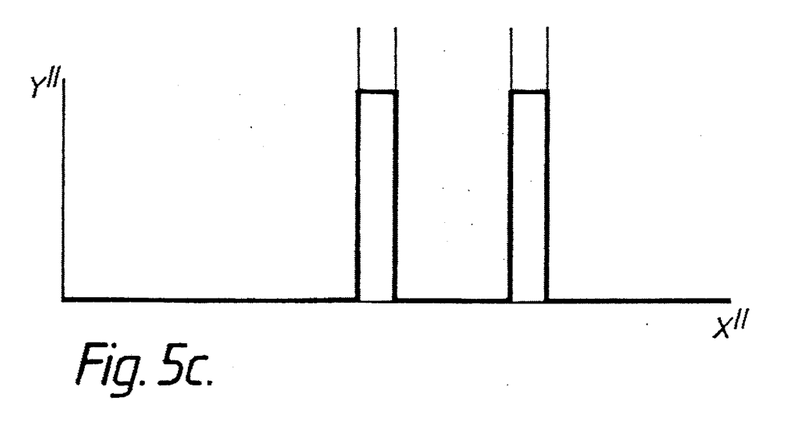
Figure 6A:
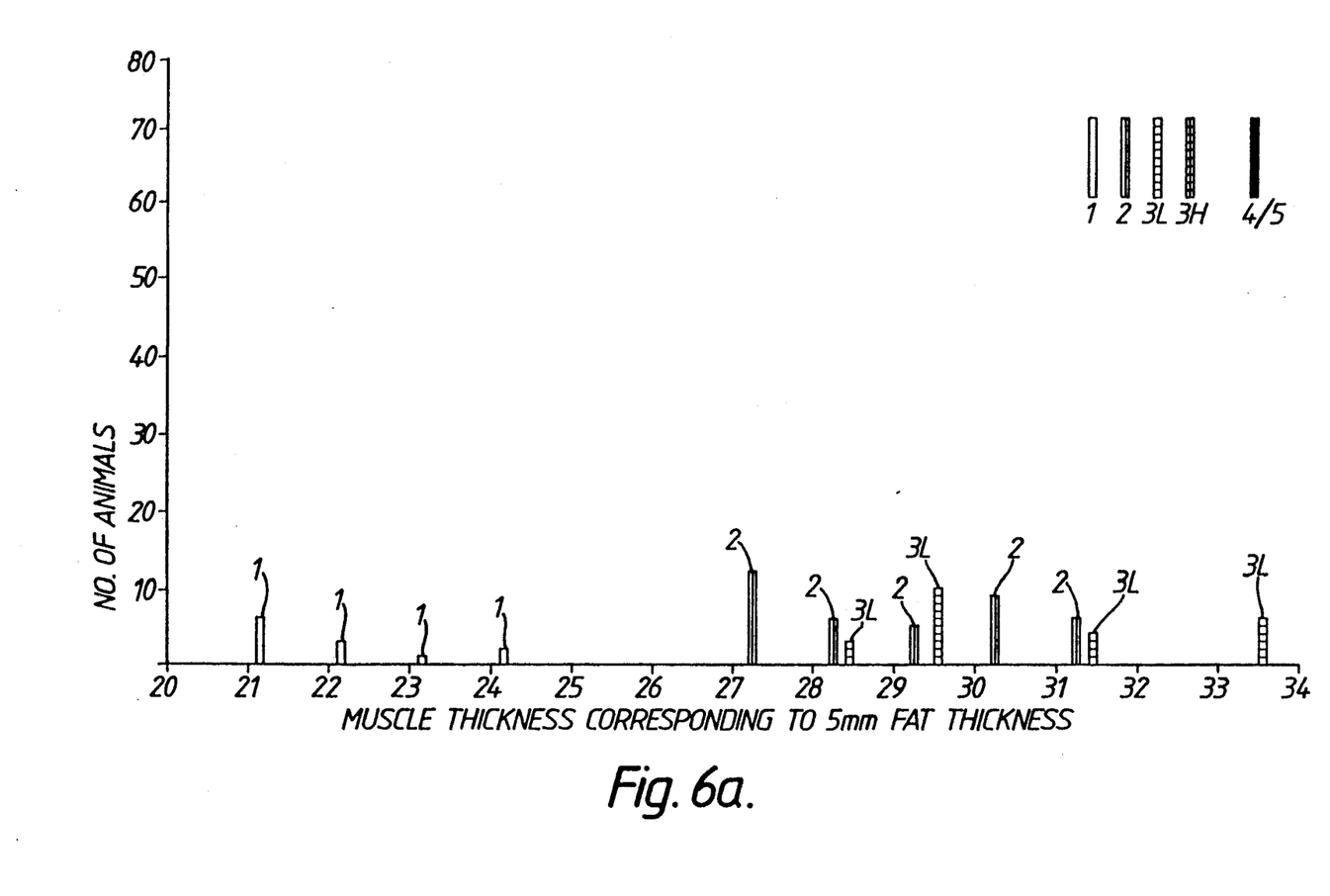
FIGS. 6a to 6e are histograms showing for different fat depths as exist at locations at different distances from the spine, numbers of animals researched found to have particular muscle thickness at such locations.
Figure 6B:
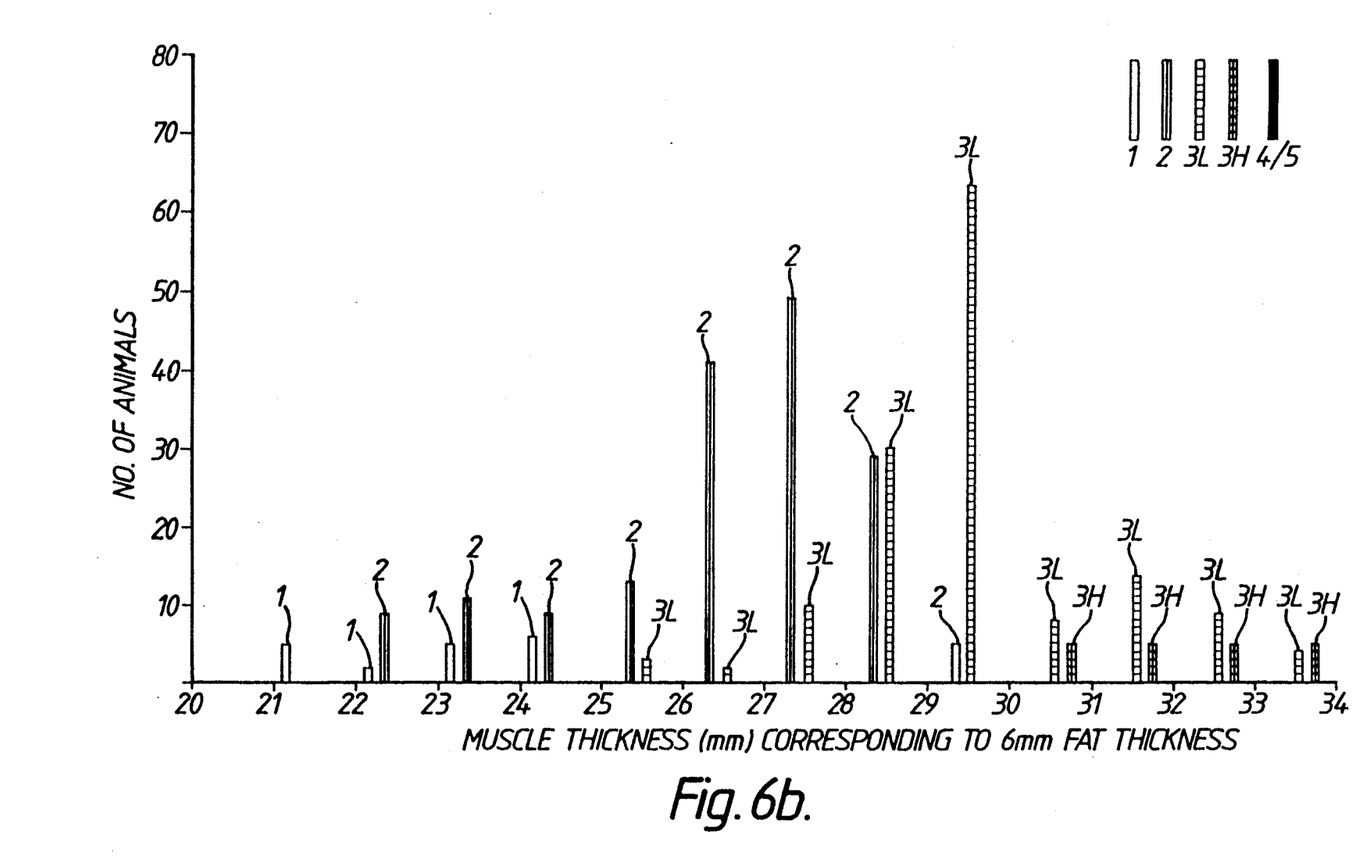
Figure 6C:
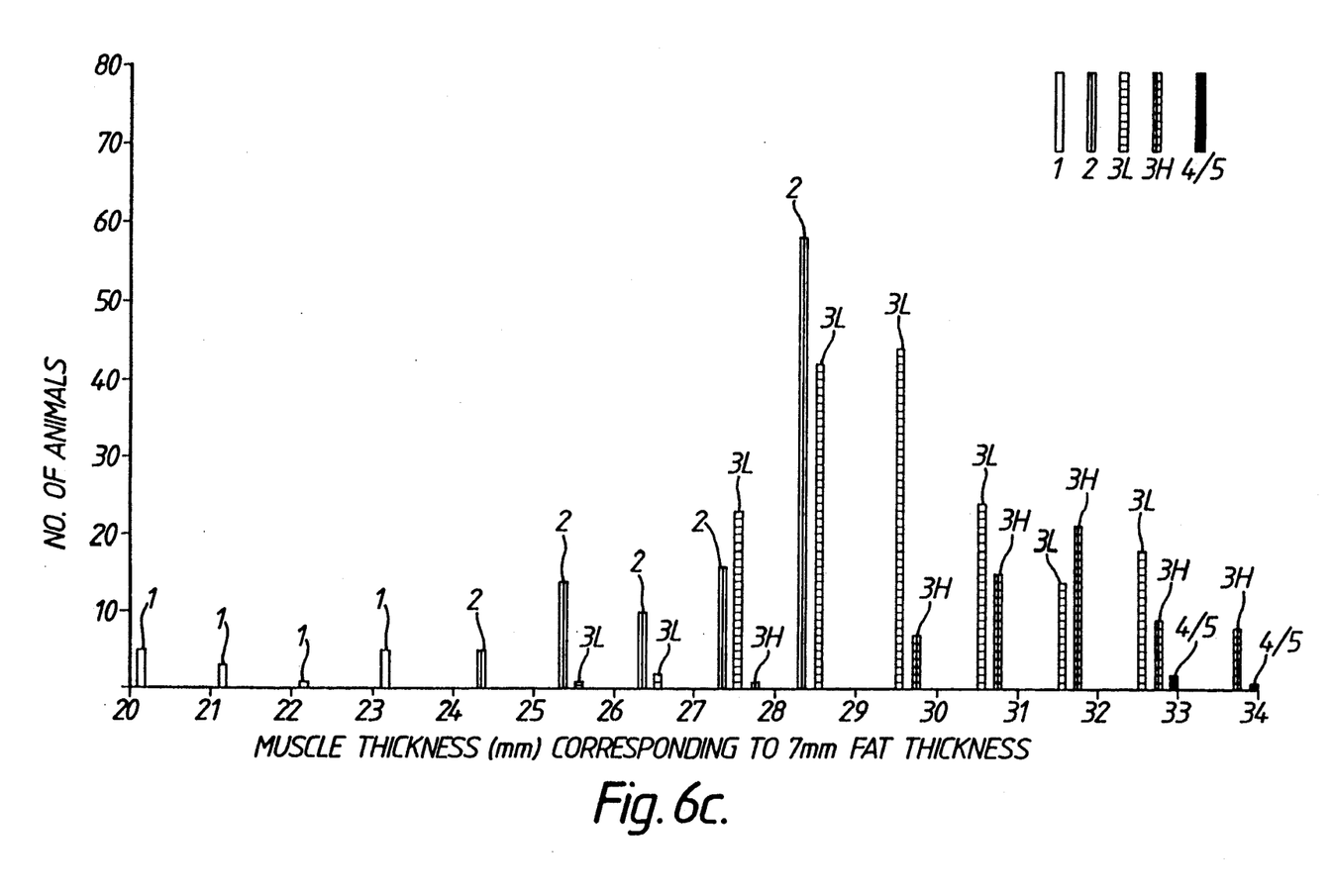
Figure 6D:
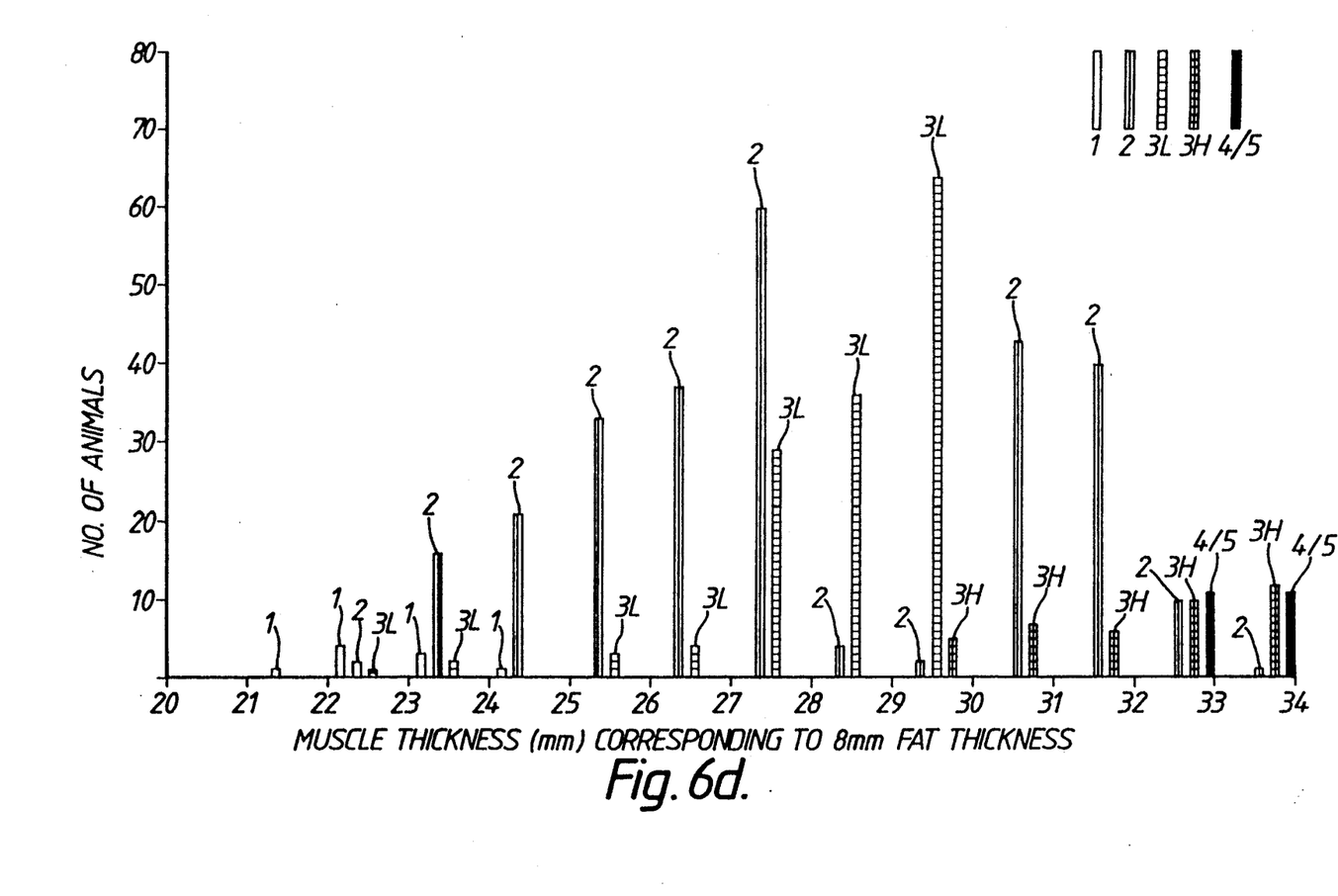
Figure 6E:
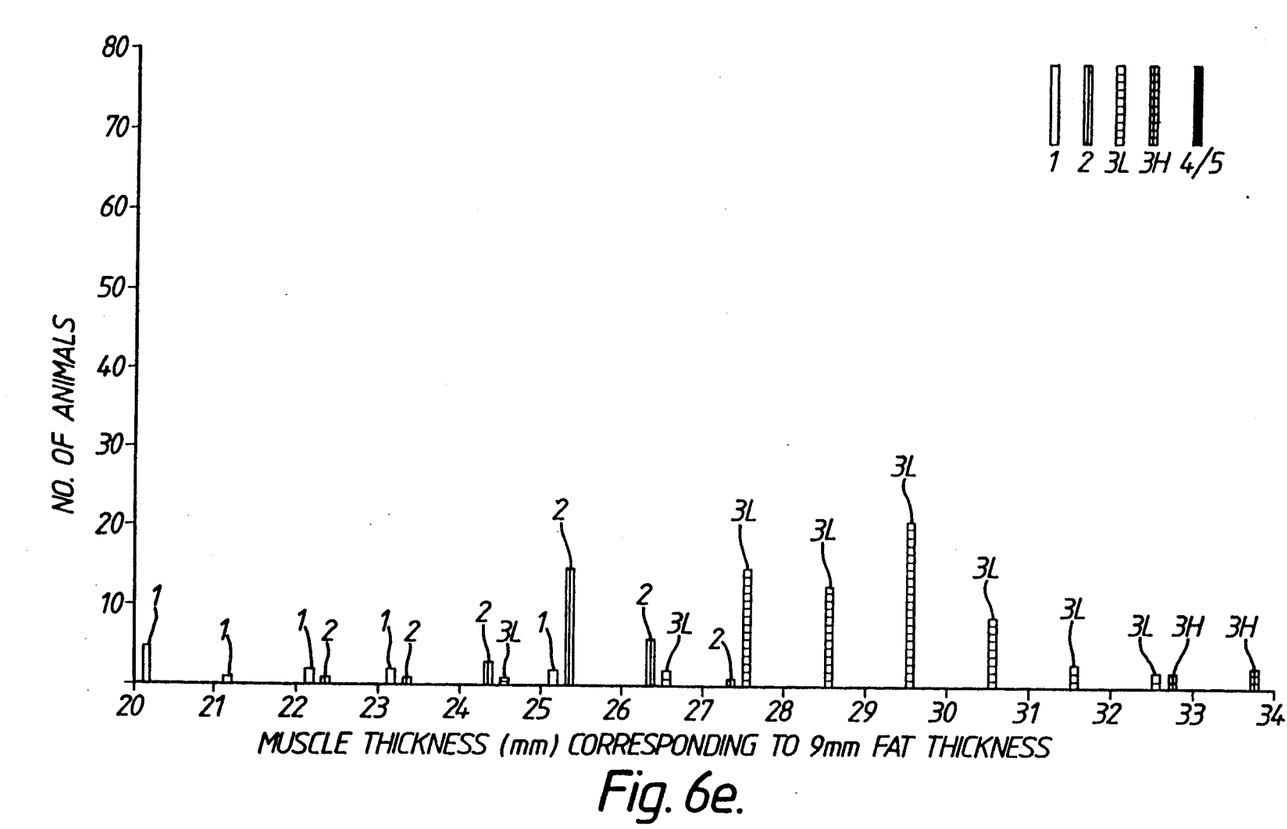

It is possible to obtain a measure of fat thickness and muscle thickness in the eye region at a position which the probe has operated merely by taking measurements directly off the photograph of FIG. 4a. However a more sophisticated form of result is obtained when automatic processing of data making up FIG. 4a is carried out. This will yield results of the type shown in FIGS. 5a, 5b and 5c. FIG. 5a is similar to FIG. 4a but in fact is turned through 90° therefrom and does not show the reflections appearing lower in the photograph of FIG. 4a. The regions in the ultrasonic image thus occur in turn along what is effectively the X direction, each extending upwardly in the Y direction. Automatic processing of the image will consist of four principle steps. The first is to scan each row (i.e. Y direction marked in FIG. 5a) of the image to determine the mean gray value $$G_y = \sum_{x=1}^{N_C} G_{yx}/N_C$$

where $G_y$ is the mean gray value of the $y^{th}$ row, $G_{yx}$ is the gray value of the $x^{th}$ column of the $y^{th}$ row and $N_C$ is the total number of columns in the image. The mean gray value function is plotted in FIG. 5b and labelled "raw data". This step may be performed on a subset of the available image data in order to reduce the processing time required.

The second step in the processing consists of smoothing the mean gray value function in order to eliminate high frequency variations. This takes the form of a simple recursive filter:

$$G_{yf} = (G_{y-1} + G_y + G_{y+1})/3$$

where $G_{yf}$ is the filtered mean value at row y. The result of this operation is also shown in FIG. 1(b) and is labelled "smoothed data".

The data is then thresholded at a value determined by the dynamic range of the smoothed data. This results in the binary image illustrated in FIG. 5c. Suitable edge de-emphasis is applied to eliminate spurious artifacts at extremes of the image.

The next step of processing the data obtained from the image involves computing the thickness of the fat and muscle layers by noting the number of rows spanned by the "white" regions of the image. The white regions correspond to the fat and bone layers in turn because these both cause substantial reflection of the incident ultrasonic wave-front. The depths of these various layers are then computed from knowledge of the scan resolution and the ultrasonic transducer characteristics against standards originally attained with carcases.

In optional additional steps, a measure of the fat content of muscle tissue based on further analysis of the ultrasonic image is computed. For this purpose, the muscle layer is segmented into regions of similar density by establishing a suitable gray scale threshold within the region previously identified. The ratio of the area of the low density (darker) regions to the higher density (brighter) regions in a representative portion of the image provides an indication of the percentage of fatty tissue in the muscle layer. Grading of carcases or animals can be carried out using standard data from scans carried out on carcases of animals of known fat content in like muscle tissue. This information can be combined with that previously obtained (depths of respective fat and bone layers on the one hand and muscle layers on the other hand) to produce an overall animal grade.

Referring finally to FIGS. 6a to 6e of the accompanying drawings, there is shown in each a summary of grading results obtained by experiment and used in calculating expected carcase grade from fat and muscle measurements in the lumbar region of live meat animals. Muscle thickness is plotted against population at each fat depth with number of animals on the X co-ordinate against muscle measure in millimeters on the Y coordinate.

FIGS. 6a to 6e also place the respective animals having the indicated muscle thickness in their carcase grades as determined conventionally subsequently after slaughter so that a complete population/grade profile can be established from the figures. The columns are captioned by numbers indicating the grade of carcase which animals having particular muscle: fat ratios possess. The grading follows a typical system adopted in the United Kingdom with 1 denoting too little muscle in relation to fat, i.e. a reject grade, 2, 3L and 3H denoting acceptable grades and 4 and 5 denoting reject grades of animals which are too lean.

When processing data such as that shown in FIGS. 6a to 6e, the normal distribution curves of each grade are plotted and the standard deviation from the mean of each is calculated. The separation of these mean values for each grade allows the back calculation of the grade from the fat and muscle measurements within a given weight, breed and species range. The same calculations apply to live animals and carcase evaluation, with only the actual measurements differing. In making the measurements summarized in FIGS. 6a to 6e:

Fat Depth = All matter between the skin and the start of the muscle layer. (In skinned carcases only fat is left).

Muscle Depth = All matter between the lower edge of the fat layer and the bone of the transverse process of the lumbar vertibrae.

Site of measurement is in the thoraco-lumbar region, at a standard position.

What is claimed is:

1. A method of carrying out the ultrasonic scanning of live animals and carcases for determining fat and muscle thickness and/or fat content of muscle, which comprises utilizing a single elongate ultrasonic scanning probe to effect scanning of a region along the back of the animal or carcase along a line parallel to the line of the spine to provide a continuous two-dimensional image extending lengthwise of said back.

2. A method as claimed in claim 1 wherein scanning is effected over eye muscle of the animal or carcass in the lumber region of the spine.

3. A method for measuring the fat and muscle thickness of live animals and carcases for the purpose of grading which comprises the steps of:
   1) scanning a region along the back of animal or carcase along a line parallel to the backbone of the animal or carcase over the eye muscle along the thickest part thereof using an elongate scanning probe;
   2) forming and capturing a continuous two-dimensional image of a region thus scanned extending lengthwise of said back in said region thus scanned;
   3) processing said image to identify the thickness of the skin and fat layer and the muscle layer there adjacent; and
   4) computing a Fat Class to be used as a factor for carcase classification in conjunction with animal weight, age, sex and conformation.

4. A method as claimed in claim 3, wherein there is computed a Fat Class which is based on both data concerning thickness of skin and fat layer and the muscle layer there adjacent and data concerning muscle fat content.

5. A method of measuring the fat content of the muscle of live animals and carcases for the purposes of grading which comprises the steps of:
   1) scanning a region along the back of the animal or carcase along a line parallel to the backbone of the animal or carcase over the eye muscle along the thickest part thereof using an elongate scanning probe;
   2) forming and capturing a continuous two-dimensional image of a region thus scanned extending lengthwise of said back in said region thus scanned;
   3) segmenting a representative areas of the muscle into regions of similar density; and
   4) determining the ratio of low density areas to higher density areas as an indication of the percentage of fat in the muscle.

6. A method as claimed in claim 5, wherein fat content percentage data for step (4) is utilized to compute a Fat Class to be used as a factor for carcase classification in conjunction with animal weight, age, sex and conformation.

7. A method as claimed in claim 6 wherein there is computed a Fat Class which is based on both data concerning thickness of skin and fat layer and the muscle layer there adjacent and data concerning muscle fat content.

8. Apparatus for carrying out the ultrasonic scanning of live animals and carcases for determining fat and muscle thickness and/or fat content of muscle which comprises an ultrasonic probe of elongate form for scanning a region of the back of the animal or carcase along a line parallel to the backbone of animal or carcase over the eye muscle along the thickest part thereof to provide a continuous two-dimensional image extending lengthwise of said back, and a computer operatively associated therewith, the computer including first means to evaluate the results of scanning for fat and muscle depth and/or fat content of muscle parallel to the backbone of an animal or carcase and over the eye muscle along the thickest part thereof, second means to compare the results obtained by said first means with standard results for like animal weight, age, sex and conformation to provide a grading of the animal in accordance with an evaluation achieved by said second means and third means for storing and/or for reproducing data received from the scanner and/or for displaying the result of an evaluation achieved by said first means.

9. Apparatus as claimed in claim 8, wherein the computer includes means to segment a representative scanned area of muscle into regions of similar density and to compute the ratio of low density areas to higher density areas as an indication of the percentage of fat in the scanned area of muscle.

10. Apparatus as claimed in claim 9, wherein the computer includes means to compute a Fat Class which is based on both data concerning thickness of skin and fat layer and the muscle layer there adjacent and data concerning muscle fat content.

11. Apparatus as claimed in claim 8, wherein the computer includes means to compute a Fat Class which is based on both data concerning thickness of skin and fat layer and the muscle layer there adjacent and data concerning muscle fat content.

12. Apparatus as claimed in claim 8, comprising means for reproducing an ultrasonic scan as a visible, continuous two-dimensional image and means for optically scanning the image at a series of rows extending through the depth of the image, which means is in operative association with the computer which comprises;
   a) means to determine the gray value of the optical scan;
   b) means to smooth the mean gray value to eliminate high frequency variations;
   c) means to threshold the data obtained at a value determined by the dynamic range of the smoothed data to produce a binary image;
   d) means to process the data from the optical image to identify the number of ultrasonically scanned rows spanned by areas of the binary image corresponding either to fat and bone layers or to muscle layers;
   e) means to compute the depth of said layers from data held by a memory of the computer comprising scan resolution and ultrasonic transducer characteristics; and
   f) means to compare the layer depths against standards attained with carcases as a measure of the grade of animal or carcase ultrasonically scanned.

* * * * *

UNITED STATES PATENT AND TRADEMARK OFFICE
CERTIFICATE OF CORRECTION

PATENT NO. : 5,208,747
DATED : May 4, 1993
INVENTOR(S) : WILSON et al.

It is certified that error appears in the above-identified patent and that said Letters Patent is hereby corrected as shown below:

```
In column 6, line 63, for "vertibrae" read --vertebrae--.
In column 7, line 9, for "lumber" read --lumbar--.
In column 7, line 43, after "segmenting" delete "a".
In column 7, line 55, for "thickness" read --thicknesses--.
```

Signed and Sealed this

First Day of March, 1994

Attest:

BRUCE LEHMAN

Attesting Officer

Commissioner of Patents and Trademarks